United States Patent [19]
Hangartner et al.

[11] 4,137,329
[45] Jan. 30, 1979

[54] INSECTICIDAL PROPARGYL ETHERS

[75] Inventors: Walter Hangartner, Schöfflisdorf; Albert Pfiffner, Bülach, both of Switzerland

[73] Assignee: Hoffmann-La Roche Inc., Nutley, N.J.

[21] Appl. No.: 830,924

[22] Filed: Sep. 6, 1977

Related U.S. Application Data

[63] Continuation of Ser. No. 606,806, Aug. 22, 1975, abandoned.

[30] Foreign Application Priority Data

Aug. 30, 1974 [CH] Switzerland ............... 11834/74

[51] Int. Cl.$^2$ ............................................. A01N 9/24
[52] U.S. Cl. ..................................... 424/342; 568/616

[58] Field of Search ................... 424/342; 260/615 R

[56] References Cited
PUBLICATIONS

Bowers, "Inter. Conf.-Insecticides for the Future", The Rockefeller Foundation, Bellagio, Italy, Apr. 22-27, 1974, Hormone Position Paper on Novel Chemicals and Targets.

Primary Examiner—V. D. Turner
Attorney, Agent, or Firm—Jon S. Saxe; Bernard S. Leon; William H. Epstein

[57] ABSTRACT

The use of dipropargyl ethers for combatting insects such as aphids, flys and mites including insecticidal compositions for such uses.

5 Claims, No Drawings

INSECTICIDAL PROPARGYL ETHERS

This is a continuation of application Ser. No. 606,806, filed Aug. 22, 1975, now abandoned.

SUMMARY OF INVENTION

Inaccordance with this invention it has been discovered that dipropargyl ethers of the formula:

$$CH\equiv C-CH_2-O-(CH_2)_n-O-CH_2-C\equiv CH \qquad I$$

wherein n is an integer from 8 to 12
are useful against insects such as aphids, whiteflies and mites. This finding was surprising in view of the fact that the compounds of formula I, as disclosed by Dr. William Bovers in a lecture delivered at the First Zoecon Conference in Palo Alto, Calif. on Apr. 3 – Apr. 6, 1972, were relatively inactive as an insect hormone agent against Tenebrio Molitor (yellow mealworm). Therefor it was completely unexpected to find that there dipropargyl ethers were active as insecticides against insects such as aphids, flys and mites.

DETAILED DESCRIPTIon

The propargyl ethers of formula I above are manufactured by following processes:
(a) reacting a compond of the formula $$X-(CH_2)_n-X' \qquad II$$

werein X and X' individually are a chlorine, bromine, iodine, mesyloxy or tosyloxy and n is as above,
with a least 2 moles of an alcoholate of the formula $$M^{\oplus} \ ^{\ominus}O-CH_2-C\equiv CH \qquad III$$

wherein $M^{\oplus}$ is an alkali metal or alkaline earth metal ion, or
(b) reacting a compound of the formula $$M^{\oplus} \ ^{\ominus}O-(CH_2)_2-O \ ^{\ominus}M^{\oplus} \qquad IV$$

wherein $M^{\oplus}$ and n are as above, with a compound of the general formula $$X-CH_2-C\equiv CH \qquad V$$

wherein X is as above.

According to embodiment (a) of the foregoing processes, the reaction of a compound of formula II with an alcoholate of formula III is carried out in an inert organic solvent, preferably in dimethylformamide, dioxane, hexamethylphosphoric acid triamide, tetrahydrofuran or dimethoxyethane or in a mixture of two or more of these solvents. The reaction is expediently carried out using the alcohol corresponding to the alcoholate of formula III in the presence of an alkali metal or an alkaline earth metal, a corresponding hydride or amide or an alkali metal hydroxide. In this manner, the alcoholate of formula III is formed from the alcohol. Preferred alkali metals are sodium and potassium and preferred alkaline earth metals are calcium and magnesium. The temperature at which the reaction is carried out is of no particular significance. The reaction can be carried out conveniently at between 0°–20° C and the boiling point of the reaction mixture. It is preferred to carry out the reaction at 50°–70° C, especially when a compound of formula II in which X and X' each represent a bromine atom is used.

The reaction of a compound of formula IV with a compound of formula V in accordance with embodiment (b) of the process is carried out under the same conditions as described earlier in connection with embodiment (a) of the process.

An especially preferred propargyl ether of formula i is 1,10-bis(2-propynyloxy)-decane.

The dipropargyl ethers of formula I are practically nonpoisonous to vertebrates. The toxicity of the dipropargyl ethers of formula I lies at over 1000 mg/kg body weight. Moreover, these dipropargyl ethers are readily degraded. The risk of a cumulation is therefore excluded. The dipropargyl ethers of formula I can accordingly be used for the control of insects in connection with materials such as animals, plants, textiles and foodstuffs. The term plants includs the leaves or fruits of trees, preferably fruit trees.

The dipropargyl ethers of formula I have very high activity against aphids, whiteflies and mites. Among the aphids, whiteflies and mites, that they are particularly suitable against, are the following:

| | |
|---|---|
| Trialeurodes vaporariorum | (Greenhouse Whitefly) |
| Myzus persicae | (Green peach aphid) |
| Tetranychus urticae | (Two-spotted spides mite) |
| Aphbis fabae | (Black bean aphid) |

The dipropargyl ethers of formula I above can be applied to the eggs or larvae, of the aforementioned insects or can be applied to the insect itself. The dipropargyl ethers will destroy the development of laid normal eggs and the larvae. Furthermore contacting the insects with the dipropargyl ethers of formula I, will kill the insects.

Thus, for example, 1,10-bis(2-propynyloxy)-decane exhibits a 95% activity after treatment of first instar larvae, of Trialeurodes vaporariorum at a spray concentration of 0.01% by weight and exhibits a 100% activity after treatment of eggs of this species at a spray concentration of 0.003% by weight.

The dipropargyl ethers of formula I can be used as pesticides in the form of concentrates or granulates or, together with inert carriers, in the form of sprays, acrosols or powders. Any conventional pesticidal carrier can be used in preparing pesticidal compositions containing the dipropargyl ether of formula I. For certain purposes, it may be advantageous to use emulsions, suspensions or solutions which contain emulsifiers or wetting agents. Examples of solid carriers which may be used are chalk, talc, bentonite, kaolin, diatomaceous earth, siliceous earth, fuller's earth, lime, gypsum, powder and dust from organic waste products, polymers (e.g., polyvinyl chloride, polyethylene, polyacrylate, polystyrene and mixed polymerisates) etc. The pesticidal compositions can also contain additives such as, for example, antioxidants, U.V. absorbers and other stabilizers as well as odorants, attractants etc. The compositions can be produced in forms which release the active ingredient in dosed amounts such as, for example, microcapsules, coated granulates, solutions in polymeric materials etc. It will be appreciated that the foregoing is given by way of exemplification only and is not intended to limit the invention in any respect.

In general, the pesticidal compositions can be formulated according to the procedures which are described, for example, in Farm Chemicals, Volume 128, page 52 and in subsequent pages. The pesticidal compositions can also contain other additives such as emulsifiers or masking agents.

The pesticidal compositions can be made in the form of concentrates which are suitable for storage and transport. Such concentrates can obtain, for example, 40-90% by weight of a dipropargyl ether of formula I. These concentrates can be diluted with the same or different carriers to provide concentrations which are suitable for practical use. In a ready-for-use pesticidal composition (e.g., one to be sprayed), concentrations of 0.01-0.5% by weight, preferably 0.1%, by weight of a dipropargyl ether of formula I can, for example, by present. The concentration can, however, also be smaller or larger.

The pesticidal compositions can be used against pests according to the usual methods; for example, by contact with or by intake into the locus to be protected i.e. animals, plants, foodstuffs, textiles, etc.

It will accordingly be appreciated that the present invention also includes within its scope (a) a pesticidal composition which contains as an essential active ingredient or essential active ingredients one or more of the dipropargyl ethers of formula I in association with an inert carrier and (b) a method of rendering a locus subject to or subjected to attack by pests free from such attack by applying to said locus a pesticidal composition, as hereinbefore defined, of one or more of the dipropargyl ethers of formul I. In applying the compound of formula I above to the locus to be protected, the compound is generally applied in an amount of from $10^{-2}$ to $10^{-8}$ g/cm$^2$ of the locus to be protected. Among the compounds of formula I are the following:

1,12-bis(2-propynyloxy)-dodecane;
1,8-bis(2-propynyloxy)-octane;
1,9-bis(2-propynyloxy)-nonane;
1,11-bis(2-propynyloxy)-undecane; and
1,10-bis(2-propynyloxy)-decane.

The following Examples illustrate the process provided by the present invention. The ether in the following examples is diethyl ether and Nujol is pure parrafin oil:

EXAMPLE 1

52.4 g of a 55% by weight sodium hydride/Nujol suspension are washed twice with hexane in order to remove the Nujol and covered with 170 ml of absolute dimethylformamide. 81 g of propargyl alcohol are added while cooling with ice. The mixture is then stirred at room temperature for 2 hours. A solution of 150 g of 1,10-dibromodecane in 500 ml of absolute dimethylformamide is then added dropwise, the mixture stirred for 1.5 hours at an internal temperature of 70° C, cooled, poured into ice-water and exhaustively extracted with hexane. The combined hexane extracts are washed neutral with water, dried over sodium sulphate, evaporated and the residue purified by chromatography on silica gel using hexane/ether (95:5). There is obtained pure 1,10-bis(2-propynyloxy)-decane which boils at 128°-130° C/0.3 mmHg; $n_D^{20} = 1.4606$.

EXAMPLE 2

30.6 g of a 55% by weight sodium hydride/Nujol suspension are washed twice with hexane in order to remove the Nujol and covered with 100 ml of absolute tetrahydrofuran. 71 g of 1,12-dodecanediol in 900 ml of absolute tetrahydrofuran are added dropwise and the mixture is stirred for 1.5 hours at 55° C. 100 g of propargyl bromide and 280 ml of hexamethylphosphoric acid triamide are added at room temperature and the mixture obtained is stirred for 18 hours at 55° C. The mixture is then cooled, poured ito ice-water, exhaustively extracted with hexane, the combined hexane extracts washed with 2-N aqueous hydrochloric acid and water, dried over sodium sulphate and evaporated. The residue is chromatographed on silica gel using hexane/ether (95:5 points by value) to give pure 1,12-bis(2-propynyloxy)dodecane of boiling point 124°-126° C/0.001 mmHg; $n_D^{20} = 1.4613$.

The following Examples illustrate typical insecticidal compositions provided by the present invention:

EXAMPLE A

An emulsifiable concentrate is prepared by mixing the following ingredients:

500 g of 1,10-bis(2-propynyloxy)-decane
80 g of nonylphenoxy-poly(ethyleneoxy)ethanol
20 g of calcium dodecylbenzenesulphonic acid and making the mixture up to 1 liter with xylene. This concentrate is diluted with water to the desired concentration and can then be sprayed.

EXAMPLE B

A spray-powder is prepared by mixing the following ingredients (the percentages stated being percentages by weight):

25% of 1,10-bis(2-propynyloxy)-decane
30% of sodium lignosulphonate
3% of sodium dodecylbenzenesulphonic acid
1% of hexamethylenetetramine
6% of magnesium carbonate (precipitated)
30% of kaolin.

This spray-powder is dispersed in water. For example, by dispersing 4 g of this spray-powder in 1 liter of water there is obtained a spray-composition which contains 0.1% by weight of 1,10-bis(2-propynyloxy)-decane.

EXAMPLE C

Bean plants carrying well developed leaves were infected with 10 adult females of Tetranychus urticae for laying eggs on the leaves. Seven days later, the leaves were treated to the run off point with an acetone solution containing 1,10-bis(2-propynyloxy)-decane at a given dose level as indicated in the following table and the activity of each dose level was determined 7 days later by calculating the % of the layed eggs which do not hatch. A control was run with pure acetone. The results are given in the following table

| Dose % by weight of active ingredient in acetone solution | % of eggs unhatched |
| --- | --- |
| 0.1 | 100 |
| 0.1 | 100 |
| 0.1 | 100 |
| 0.03 | 100 |
| 0.03 | 100 |
| 0.03 | 98 |
| 0.01 | 56 |
| 0.01 | 63 |
| 0.01 | 81 |

| Dose % by weight of active ingredient in acetone solution | % of eggs unhatched |
|---|---|
| control | 0–3% |

EXAMPLE D

Determination of ovicidal activity

Bean plants carrying 2 well developed leaves were placed in a Greenhouse whitefly (Trialeurodes vaporariorum) breeding cage for 1 to 3 days in order to obtain a homogeneous oviposition. After oviposition, the leaves were sprayed on both sides with an acetone solution containing 0.01% by weight of 1,10-bis(2-propynyloxy)decane and as a control pure acetone. In determining the ovicidal activity the % reduction of the hatching rate in comparison with the control was calculated 7 days after treatment. For this compound at a dose of 0.003%, the % reduction was 100%.

EXAMPLE E

Determination of Larvicidal activity

Bean plants carrying 2 well developed leaves were placed in a whitefly breeding cage (Trialeurodes vaporariorum) for 1 to 3 days in order to obtain a homogeneous oviposition. Seven days after oviposition when the eggs hatched into larvae, the leaves were sprayed to the run off point on both sides with an acetone solution containing 0.01% by weight of 1,10-bis (2-propynyloxy)decane. Other larvae containing bean plants were treated in the same manner with pure acetone as a control. In determining the larvicidal activity, seven days after spraying, the larval mortality was determined. The mortality rate was calculated as % mortality of the larvae in comparison with the control. The mortality rate of the 0.01% acetone solution of the above compound was approximately 91 to 95%.

We claim:

1. A process for protecting materials from pests selected from the group consisting of aphids, whiteflies and mites comprising applying to the material to be protected a pesticidally effective amount of a composition containing as an active ingredient a compound of the formula:

$$CH{\equiv}C-CH_2-O-(CH_2)_n-O-CH_2-C{\equiv}CH$$

where $n$ is an integer of from 8 to 12 or mixtures thereof and an inert pesticidal carrier.

2. The process of claim 1 wherein said material is a foodstuff, animal, textile or plant.

3. The process of claim 1 wherein the composition is applied to the material in an amount sufficient to supply said active ingredient in an amount of from about $10^{-2}$ to $10^{-8}$ grams/cm$^2$ of the material to be protected.

4. The process of claim 3 wherein said active ingredient is 1,12-bis(2-propynyloxy)-dodecane.

5. The process of claim 3 wherein said active ingredient is 1,8-bis(2-propynyloxy)-octane.